United States Patent
Ito et al.

[11] Patent Number: 5,968,479
[45] Date of Patent: Oct. 19, 1999

[54] DIAGNOSTIC MARKER

[75] Inventors: Susumu Ito, Tokushima; Masayuki Nozawa, Chiba; Masanobu Shiga, Kumamoto; Kazumi Sasamoto, Kumamoto; Kazuhiro Takesako, Kumamoto; Hiroshi Takeuchi, Chiba, all of Japan

[73] Assignee: Daiichi Pure Chemicals Co., Ltd., Tokyo, Japan

[21] Appl. No.: 08/875,398

[22] PCT Filed: Jan. 30, 1996

[86] PCT No.: PCT/JP96/00169

§ 371 Date: Sep. 17, 1997

§ 102(e) Date: Sep. 17, 1997

[87] PCT Pub. No.: WO96/23525

PCT Pub. Date: Aug. 8, 1996

[30] Foreign Application Priority Data

Jan. 30, 1995 [JP] Japan ....................... 7-12283
Aug. 31, 1995 [JP] Japan ....................... 7-223613

[51] Int. Cl.⁶ ............... A61K 49/00; A61K 39/395; G01N 33/00; C07D 209/60
[52] U.S. Cl. ............... 424/9.6; 424/178.1; 424/179.1; 424/801; 424/802; 435/960; 435/968; 436/86; 436/94; 436/172; 436/517; 436/800; 600/317; 548/156; 548/455; 548/465
[58] Field of Search .................. 424/9.6, 178.1, 424/179.1, 801, 802; 436/800, 517, 547, 86, 94, 172; 430/93; 546/152, 165; 548/156, 455, 465; 435/287.2, 960, 968; 514/1, 44; 600/317

[56] References Cited

U.S. PATENT DOCUMENTS 5,627,027  5/1997  Waggoner .................. 435/6

FOREIGN PATENT DOCUMENTS

| 6118081 | 4/1994 | Japan . |
| 6222059 | 8/1994 | Japan . |
| 7-83925 | 3/1995 | Japan . |
| 7103983 | 4/1995 | Japan . |
| 9200106 | 1/1992 | WIPO . |
| 9502699 | 1/1995 | WIPO . |

OTHER PUBLICATIONS

Shikoku Acta Medica, vol. 29, No. 2, 1973, pp. 108–188.
Gastrointestinal Endoscopy, vol. 34, No. 10, 1992, pp. 2287–2296.
Gastrointestinal Endoscopy, vol. 40, No. 5, 1994, pp. 621–628.
An English Language Abstract of JP 7–103983, Apr. 1995.
An English Language Abstract of JP 7–83925, Mar. 1995.
An English Language Abstract of JP 6–222059, Aug. 1994.
An English Language Abstract of JP 6–118081, Apr. 1994.
Tempelman et al., "Use of Cyanine Dyes with Evanescent Wave Fiber Optic Biosensors" Proc. SPIE–Int. Soc. Opt. Eng., 2293, pp. 139–148, 1994.

Primary Examiner—Jose' G. Dees
Assistant Examiner—Michael G. Hartley
Attorney, Agent, or Firm—Greenblum & Bernstein P.L.C.

[57] ABSTRACT

A diagnostic marker containing (a) a detection system such as an antibody and (b) a fluorescent functional group that is bound to the detection system and represented by the following formula:

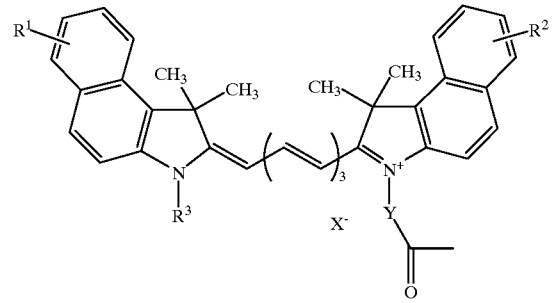

wherein $R^1$ and $R^2$ independently represent hydrogen atom, an alkyl group or the like; $R^3$ represents an alkyl group, a sulfonic acid-alkyl group or the like; $X^-$ represents an anion species, if required; Y represents a $C_1$–$C_{10}$ alkylene group or a $C_1$–$C_{10}$ alkylene group containing one or more atoms selected from the group consisting of oxygen atom, nitrogen atom and sulfur atom. The diagnostic marker emits fluorescence having a wavelength of 780 nm or more when irradiated with near or far infrared rays, and thus useful for infrared endoscopic diagnosis or identification of a focus in surgical operation.

24 Claims, 3 Drawing Sheets

DIAGNOSTIC MARKER

FIELD OF THE INVENTION

The present invention relates to a diagnostic marker. More specifically, the present invention relates to a diagnostic marker which rarely cause histological disorder and are applicable to a living body, characterized in that an antibodies or other that specifically recognizes tumor cells and the like is bound to a specific labeling compound that is excited and emits fluorescence when irradiated with near infrared rays or far infrared rays.

BACKGROUND ART

In recent years, endoscopic diagnosis has easily been conducted with the spread of electronic endoscopes, and it becomes possible to infallibly find stomach cancer or large bowel cancer as initial cancers. However, as far as the diagnosis of microcarcinoma is concerned, almost the same levels of diagnostic performance are achieved by an electronic endoscope and an ordinary endoscope. The fact means that new diagnostic methods that can efficiently function electronic endoscopes have not yet been established. If microlesions can be marked with a labeling antibody that is detectable under electronic endoscopy, it may be possible to easily detect microlesions, such as those not recognizable by an ordinary endoscope, with imaging through a computerized process. However, such method has not yet been practically used.

In order to establish a method utilizing an electronic endoscope such as described above, it is necessary to directly stain a living tissue by means of an immuno-histochemical staining method. Staining methods for fixed specimens are established techniques. However, a staining method for non-fixed specimens has not yet become a technique available to those skilled in the art. For example, although an immuno-staining method for non-fixed specimens was reported [Shikoku Acta Medica, Vol. 29, No. 2, pp. 180–188, 1973], no immuno-staining method for an excised fresh specimen or a living tissue, per se, that utilizes near infrared ray has been reported in this field of the art.

In addition, a diagnostic marker that is detectable under electronic endoscopy, e.g., a labeled antibody, is also required for the aforementioned diagnostic method. Diagnostic markers are known which characterized in that a labeling compound, that emits fluorescence as ultraviolet and visible light when excited with ultraviolet rays, is bound to an antibody, and they have been commonly used for the detection of cancer cells or cancer tissues that exist in tissues isolated from living bodies. However, methods utilizing fluorescent diagnostic markers that needs excitation with ultraviolet rays cannot be applied to living bodies, because ultraviolet rays may cause damages on living tissues and DNAs. No diagnostic marker that can be directly applied to a living body has been known so far.

It is known that indocyanine green (ICG) exhibits unique absorption properties and emits fluorescence under infrared ray endoscopy. Clinical cases were reported in which indocyanine green was applied when an infrared ray endoscope was used (Gastroenterological Endoscopy, 34, pp.2287–2296, 1992; and Gastrointestinal Endoscopy, 40, pp.621–2; 628, 1994). However, in these cases, ICG was intravascularly administered. Furthermore, fluorescent dyes, including indocyanine green as a typical example, have generally high hydrophobicity and are absorbed rapidly when they, per se, are administered into intestinal tract. For this reason, attempts have been made to increase their water-solubility by introducing hydrophilic groups, e.g., sulfonyl group, into ring structures or side chain moieties, and thereby improve measurement efficiency and eliminate the problem of toxicity after absorption. However, any water-soluble labeling compound has not yet been known that can emit fluorescence comparable to that of indocyanine green.

An object of the present invention is to provide a diagnostic marker useful for directly staining a living tissue by an immuno-histochemical staining method. Another object of the present invention is to provide a diagnostic marker which emits fluorescence when irradiated with near infrared rays or far infrared rays that rarely cause histological disorders, and can be directly applied to a living body. In other word, the object of the present invention is to provide a diagnostic marker which is free from problems of damages on living tissues and DNAs due to ultraviolet excitation, and can be applied to living bodies. It is also an object of the present invention to provide a diagnostic marker which has excellent water solubility as well as the features as mentioned above.

A further object of the present invention is to provide a diagnostic marker applicable to living bodies which is useful for a quasi-internal early diagnosis of malignant neoplasms in epithelial tissues, e.g., esophagus cancer, stomach cancer, or large bowel cancer, or infectious diseases by means of an infrared endoscope or other, or useful for the identification or diagnosis of a focus in a surgical operation. A still further object of the present invention is to provide a method for directly staining a living tissue by an immuno-histochemical method using a diagnostic marker as mentioned above.

DESCRIPTION OF THE INVENTION

The inventors of the present invention earnestly made efforts to achieve the foregoing objects and prepared various indocyanine green derivatives, and as a result, they succeeded in preparing indocyanine green derivatives that emit fluorescence under excitation with near infrared rays and far infrared rays. They also found that a diagnostic marker that is directly applicable to a living body can be prepared by reacting the aforementioned indocyanine green derivative, as a labeling compound, with an anti-cancer antigen-antibody and the like, and that the diagnostic marker as mentioned above is useful for a direct staining of a living tissue by an immuno-histochemical staining method.

In addition, the inventors earnestly conducted researches to provide diagnostic markers having excellent water solubility. As a consequence, they found that, among the aforementioned indocyanine green derivatives, compounds that can form an intramolecular ion pair (a zwitterion) may have reduced water solubility due to the decrease of molecular ionic property after the formation of the intramolecular ion pair, whilst these derivatives do not form intramolecular ion pair when treated with sodium iodide or other and whole molecular ionic properties are maintained, and thereby water solubilities are remarkably increased. The present invention was achieved on the basis of these findings.

The present invention thus provides a diagnostic marker which comprises (a) a detection system; and (b) a fluorescent functional group that is bound to the detection system and represented by the following formula (I):

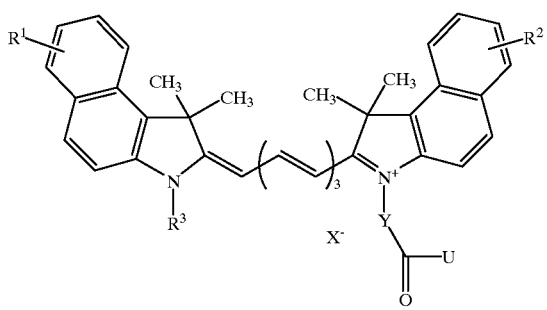

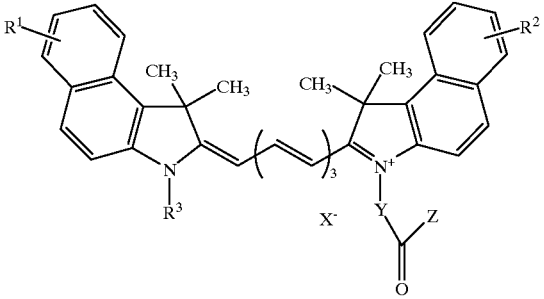

wherein $R^1$ and $R^2$ independently represent hydrogen atom, an alkyl group, an aryl group, an alkoxy group, or a sulfonic acid group; $R^3$ represents an alkyl group, a sulfonic acid-alkyl group, or an amino-substituted alkyl group; $X^-$ represents an anion species, if required; Y represents a $C_1$–$C_{10}$ alkylene group or a $C_1$–$C_{10}$ alkylene group containing one or more atoms selected from the group consisting of oxygen atom, nitrogen atom, and sulfur atom; U represents a site at which a detection system binds.

According to another embodiment of the present invention, there is provided a diagnostic marker containing (a) a detection system; and (b) a fluorescent functional group represented by the following formula (II) that is bound to the detection system:

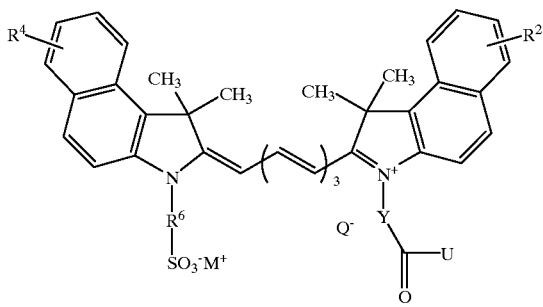

wherein $R^4$ and $R^5$ independently represent hydrogen atom, an alkyl group, an alkoxy group, or a sulfonate group; $R^6$ represents an alkylene group; $M^+$ represents an alkali metal ion; $Q^-$ represents a halogen ion, perchlorate ion, or thiocyanate ion; Y represents a $C_1$–$C_{10}$ alkylene group or a $C_1$–$C_{10}$ alkylene group containing one or more atoms selected from the group consisting of oxygen atom, nitrogen atom, and sulfur atom; U represents a site at which a detection system binds.

According to another aspect of the present invention, there are provided, as compounds useful for the manufacture of the aforementioned diagnostic markers, a compound represented by the following formula (III);

wherein $R^1$ and $R^2$ independently represent hydrogen atom, an alkyl group, an aryl group, an alkoxy group, or a sulfonic acid group; $R^3$ represents an alkyl group, a sulfonic acid-alkyl group, or an amino-substituted alkyl group; $X^-$ represents an anion species, if required; Z represents a group selected from the groups represented by the following formulas:

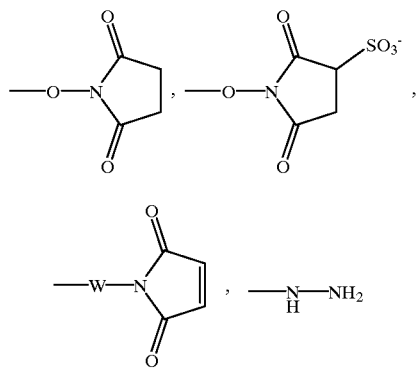

W and Y independently represent a $C_1$–$C_{10}$ alkylene group or a $C_1$–$C_{10}$ alkylene group containing one or more atoms selected from the group consisting of oxygen atom, nitrogen atom, and sulfur atom; and a compound represented by the following formula (V):

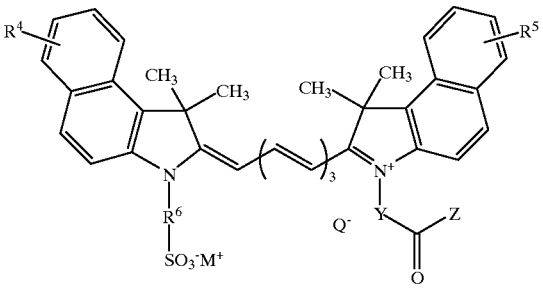

wherein $R^4$ and $R^5$ independently represent hydrogen atom, an alkyl group, an alkoxy group, or a sulfonate group; $R^6$ represents an alkylene group; $M^-$ represents an alkali metal ion; $Q^-$ represents a halogen ion, perchlorate ion, or thiocyanate ion; Z represents a group selected from the groups represented by the following formulas:

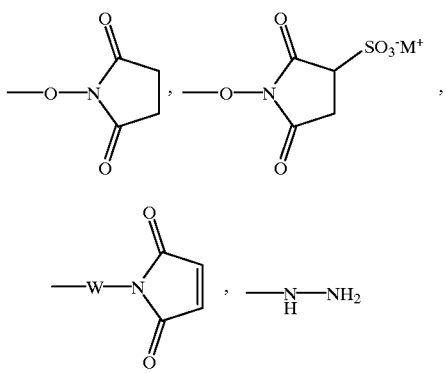

W and Y independently represent a $C_1$–$C_{10}$ alkylene group and a $C_1$–$C_{10}$ alkylene group containing one or more atoms selected from the group consisting of oxygen atom, nitrogen atom and sulfur atom. The present invention further provides a method for preparing the aforementioned diagnostic marker which comprises the step of reacting the above compound with a detection system.

There is also provided a diagnostic marker comprising (a) a detection system; and (b) a fluorescent functional group that is bound to the detection system and emits fluorescence having a wavelength of 780 nm or more when irradiated with an excitation ray having a wavelength of 600–800 nm. In addition, according to preferred embodiments of the aforementioned diagnostic markers, there are provided the above diagnostic markers wherein the fluorescent functional group is directly bound to the detection system; the above diagnostic markers wherein the fluorescent functional group is bound to the detection system by means of a linker or a protein; the above diagnostic markers wherein the detection system is selected from the group consisting of an antibody, a nucleic acid, and a substance as an amplification system; the above diagnostic markers wherein an anti-cancer antigen-antibody is used as the antibody; the above diagnostic markers which are used for an infrared endoscopic diagnosis or identification of a focus in a surgical operation; and the above diagnostic markers which are used for directly staining tissues of living bodies by immuno-histochemical staining methods. Furthermore, there is provided a diagnostic agent comprising any one of the aforementioned diagnostic markers as an active ingredient.

BEST MODE FOR CARRYING OUT THE INVENTION

Figure 1A:
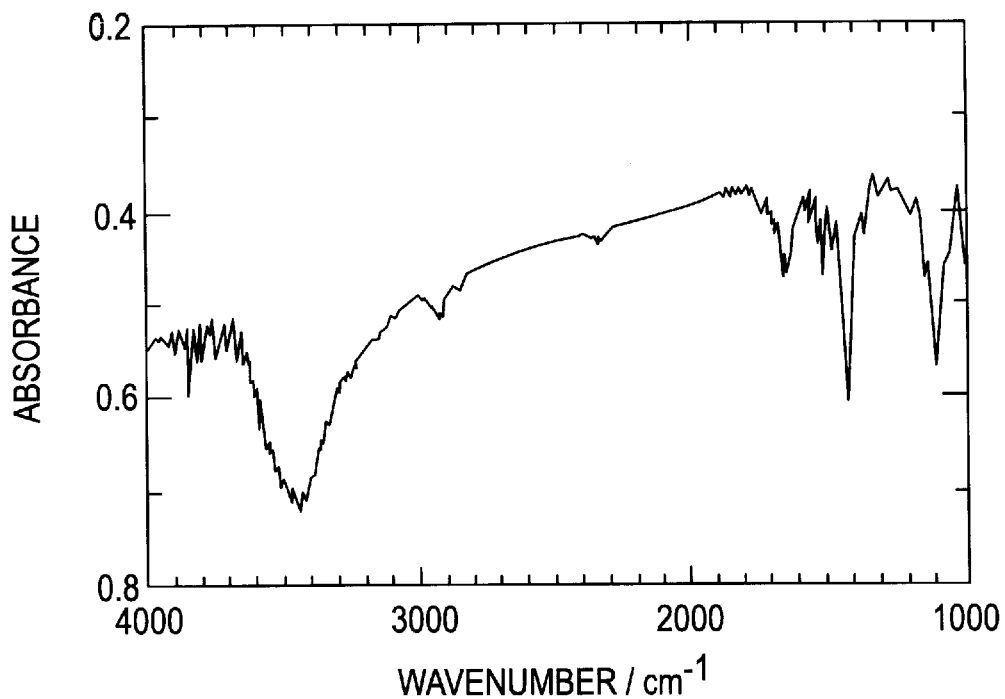
FIG. 1 shows an infrared absorption spectrum of a labeling compound (Compound 1). (A) is an infrared absorption spectrum of Compound 18 in the form of salt that was formed by the addition of sodium iodide; and (B) is an infrared absorption spectrum of indocyanine green-N-hexanoic acid sulfosuccinimide ester (Compound 17) used as a starting material.

The fluorescent functional groups represented by the above formulas (I) and (II) are bound to a detection system by means of the carbonyl group of —Y—CO— group that is attached to the ring structure. In the above formula (I), $R^1$ and $R^2$ independently represent hydrogen atom, an alkyl group, an alkoxy group, or sulfonic acid group (—$SO_3H$). Each of. $R^1$ and $R^2$ may substitute on the phenyl group at any position. As the alkyl group, a straight- or branched-lower alkyl group having 1 to 6 carbon atoms, preferably a straight- or branched-lower alkyl having 1 to 4 carbon atoms may be used. For example, methyl group, ethyl group, propyl group, isopropyl group, n-butyl group, sec-butyl group, tert-butyl group and the like are preferred.

As the aryl group represented by $R^1$ and $R^2$, phenyl group, naphthyl group, pyridyl group and the like which are substituted or non-substituted may be used. As the alkoxy group, a straight- or branched-lower alkoxy group having 1 to 6 carbon atoms, preferably those having 1 to 4 carbon atoms may be used. More specifically, methoxy group, ethoxy group, propoxy group, isopropoxy group, n-butoxy group, sec-butoxy group, tert-butoxy group and the like are preferably used. As the sulfonic acid groups, —$SO_3H$ group as the free form, or sulfonic acid groups in the form of base addition salts (sulfonate groups) such as sodium salt and potassium salt may be used. Among them, preferably examples include those wherein $R^1$ and $R^2$ independently represent hydrogen atom, an alkyl group, an alkoxy group, or a sulfonate group.

$R^3$ represents an alkyl group, a sulfonic acid-alkyl group, or an amino-substituted alkyl group. As the alkyl group in these groups, for example, those mentioned above may be used. A sulfonic acid group of the sulfonic acid-alkyl group or an amino group of the amino-substituted alkyl group may substitute at any position of the alkyl group. For example, those with substitution at the terminal of the alkyl group may preferably used.

The sulfonic acid group and the amino group may form base addition salts and acid addition salts, respectively. For example, preferable compounds include those wherein the sulfonic acid groups form sodium salts or potassium salts, or those wherein the amino groups forms salts such as ammonium halides or those wherein the amino groups are quaternized. In addition, substituted or non-substituted amino groups may be used as the amino group. Examples of the sulfonic acid-alkyl group and the amino-substituted alkyl group include sulfonic acid-methyl group (—$CH_2SO_3H$), sulfonic acid-ethyl group, aminomethyl group, aminoethyl group, methylaminoethyl group, and salts thereof.

In the fluorescent functional group represented by the formula (I), $X^-$ represents an anion species, if required, such as halogen ion, and acetate ion, perchlorate ion, and carbonate ion. The anion species represented by $X^-$ act to cancel positive charge on the nitrogen atom in the ring that is substituted with Y—CO— group, so that the fluorescent functional group represented by the formula (I) as a whole is maintained neutral. Therefore, for example, when one of the groups $R^1$, $R^2$ and $R^3$ in the fluorescent functional group represented by the formula (I) is an anionic group, $X^-$ may sometimes not be required, because the negative charge of the group cancel the positive charge on the quaternary nitrogen atom of the ring structure so as to form an intramolecular zwitterion. On the other hand, when any one of $R^1$ and $R^2$ is a sulfonic acid group and $R^3$ is an amino-substituted alkyl group, charges between these groups may be balanced, and as a result, $X^-$ may sometimes be required.

In the fluorescent functional group represented by the above formula (II), $R^4$ and $R^5$ independently represent hydrogen atom, an alkyl group, an alkoxy group or a sulfonate group. Each of $R^4$ and $R^5$ may substitute on the phenyl group at any position. As the alkyl group and the alkoxy group, those mentioned above may be used. The sulfonate group (—$SO^{3-}M^+$ wherein $M^+$ represents an alkali metal ion that may be the same as or different from $M^+$ as a counter ion for $Q^-$) may be, for example, sodium sulfonate group or potassium sulfonate group.

$R^6$ represents a straight- or branched-alkylene group. For example, a straight- or branched-lower alkylene group having 1 to 6 carbon atoms, preferably those having 2 to 5 carbon atoms, and more preferably trimethylene group, tetramethylene group, or pentamethylene group may be used. The —$SO_3^-$ group substituting on $R^6$ may bind to the alkylene group at any position. For example, those with substitution at the terminal of the alkylene group may preferably used. More specifically, a group represented by —$(CH_2)_k$—$SO_3^-$ wherein k is an integer of from 2 to 4 and the like are preferred as $R^6$—$SO_3^-$.

$M^+$ represents an alkali metal ion. As the alkali metal ion, sodium ion or potassium ion may preferably be used. $Q^-$ represents a halogen ion, perchlorate ion, or thiocyanate ion. Preferably, chlorine ion, bromine ion, or iodine ion may be used. Among them, iodine ion is particularly preferred. Although not intended to be bound by any specific theory, the aforementioned fluorescent functional group has positive charge on the nitrogen atom on which —Y—CO— group substitutes (represented as $N^+$ in the above formula) and negative charge derived from $R^3$—$SO_3^-$. Where an alkali metal salt represented by $M^+Q^-$ co-exists, ionic bondings are formed respectively between the positive charge on the nitrogen atom (represented by $N^+$ in the above formula) and $Q^-$ and between $R^3$—$SO_3^-$ and $M^+$. As a result, formation of an intramolecular pair ions is prevented, and the ionic property of the whole molecule is maintained as water solubility is remarkably increased.

In the above formulas (I) and (II), Y represents a straight- or branched-alkylene group having 1 to 10 carbon atoms, preferably a straight- or branched-alkylene group having 3 to 5 carbon atoms, and more preferably trimethylene group, tetramethylene group or pentamethylene group. Alternatively, Y represents a straight- or branched-alkyl group having 1 to 10 carbon atoms which contains one or more atoms selected from the group consisting of oxygen atom, nitrogen atom, and sulfur atom. As the group represented by —Y—CO—, for example, —$CH_2$—CO—; —$(CH_2)_2$—CO—; —$(CH_2)_3$—CO—; —$(CH_2)_4$—CO—; —$(CH_2)_5$—CO—; —$CH_2$—CO—NH—$(CH_2)_5$—CO—; —$(CH_2)_2$—CO—NH—$(CH_2)_5$—CO—; —$(CH_2)_3$—CO—NH—$(CH_2)_5$—CO—; —$(CH_2)_4$—CO—NH—$(CH_2)_5$—CO—; —$CH_2$—CO—NH—$(CH_2)_5$—CO—NH—$(CH_2)_2$—CO—; —$(CH_2)_4$—CO—(N,N'-piperadinyl)—$(CH_2)_2$—CO—("N, N'-piperadinyl" means that a piperazine is substituted with —$(CH_2)_4$—CO— at the 1-position and with —$(CH_2)_2$—Z group at the 4-position, and similarly used hereinafter in the specification.), —$CH_2$—CO—NH—$(CH_2)_5$—CO—(N,N'-piperadinyl)—$(CH_2)_2$—CO— and the like may be utilized.

The carbonyl group of —Y—CO— group may bind to a detection system by means of the Y group which may be a straight- or branched-alkylene group having 1 to 10 carbon atoms; a straight- or branched-alkylene group having 1 to 10 carbon atoms that contains one or more atoms selected from the group consisting of oxygen atom, nitrogen atom and sulfur atom; or —NH—NH— group.

Among the diagnostic markers of the present invention, for the manufacture of the diagnostic marker having the fluorescent functional group represented by the formula (I), a labeling compound of the above formula (III) may preferably be used. For the manufacture of the diagnostic marker having a fluorescent functional group represented by the formula (II), a labeling compound of the following formula (V) may preferably be used.

As the group represented by Y—CO—Z in the compounds of the above formulas (III) and (V), for example, —$CH_2$—CO—Z; —$(CH_2)_2$—CO—Z; —$(CH_2)_3$—CO—Z; —$(CH_2)_4$—CO—Z; —$(CH_2)_5$—CO—Z; —$CH_2$—CO—NH—$(CH_2)_5$—CO—Z; —$(CH_2)_2$—CO—NH—$(CH_2)_5$—CO—Z; —$(CH_2)_3$—CO—NH—$(CH_2)_5$—CO—Z; —$(CH_2)_4$—CO—NH—$(CH_2)_5$—CO—Z; —$CH_2$—CO—NH—$(CH_2)_5$—CO—NH—$(CH_2)_2$—CO—Z; —$(CH_2)_4$—CO—(N,N'-piperadinyl)—$(CH_2)_2$—Z; —$CH_2$—CO—NH—$(CH_2)_5$—CO—(N,N'-piperadinyl)—$(CH_2)_2$—Z and the like may be utilized.

As "W" in the group represented by Z, groups corresponding to Y in the exemplified Y—CO—Z as mentioned above can preferably be used. The $M^+$ as the counter ion for the sulfonic acid group of the N-sulfosuccinimidyloxy group and $M^+$ as the counter ion for $Q^-$ in the labeling compound of the formula (V) may be the same or different. It is preferred that the both of them are sodium ions. Among the aforementioned labeling compounds, compound represented by the formula (V) can be easily manufactured by, for example, preparing a compound represented by the formula (V) in the form of the pair ion wherein no alkali metal salt represented by $M^+X^-$ exists, dissolving the compound in a solvent such as dimethyl sulfoxide or dimethylformamide at a high concentration, and then adding an alkali metal salt into the solution.

Examples of the preparation of compounds of the present invention that can preferably be used for the manufacture of the diagnostic marker of the present invention will be specifically explained in Examples. It can be understood by an ordinarily skilled artisan that the compounds of the present invention can readily be prepared by referring to these examples, and appropriately modifying or altering starting compounds, reagents, reaction conditions and other.

When N-succinimidyloxy group or N-sulfosuccinimidyloxy group is used as "Z," these groups form a reactive activated ester together with the carbonyl group to which Z binds, and accordingly, the amino group ($H_2N$—R) contained in the detection system may substitute for "Z" in the activated ester to form —Y—CO—NH—R. When 2-(N-maleimide)-alkyl group is used as "Z," thiol group (HS—R) contained in the detection system may react to form —Y—CO-alkyl-S—R. When "Z" is —NH—$NH_2$, an aldehyde group (OHC—R) at the terminal of a reducing sugar contained in the detection system may react to form —Y—CO—NH—NH—CO—R.

Accordingly, by reacting a labeling compound with a detection system, the ring structure of the labeling compound represented by the formula (III) or (V) and —Y—CO— moiety as a linker binding to the ring structure are preserved as a fluorescent functional group in the diagnostic marker of the present invention. However, the diagnostic markers of the present invention having the chemical structures as mentioned above are not limited to those prepared by the aforementioned processes, and it should be understood that those prepared by any methods fall within the scope of the present invention.

As for the fluorescent functional groups represented by the formulas (I) and (II), the compounds represented by the formulas (III) and (V), and the compounds disclosed in the schemes in Examples, positive charges on the nitrogen atoms (represented as $N^+$ in the above formulas) are indicated as being localized on one of the nitrogen atoms in the ring structure just for the sake of convenience. It can readily be understood by those skilled in the art that the positive charges may be delocalized onto the other nitrogen atoms through conjugated double bonds. Therefore, it should also be noted that any tautomers due to such conjugation fall within the scope of the present invention.

As the detection system that binds to the aforementioned fluorescent functional group, antibodies recognizing various antigens such as antibodies highly specific to cancers, nucleic acids which can be used as probes, substances for amplification systems which are used in amplification systems such as biotin-avidin system or other may be used. As the antibodies, for example, anti-cancer antigen-antibodies may be used which specifically bind to cancer cells or cancer tissues, preferably to early cancer cells or early cancer tissues. For example, anti-tumor antibodies relating to stomach which specifically react with CEA, AFP, CA19-9, NSE, DU-PAN-2, CA50, SPan-1, CA72-4, CA125, HCG, p53, STN (sialyl Tn antigen), c-erbB-2 proteins and the like, and anti-tumor antibodies specifically reacting with tumor antigens of esophagus cancer, large bowel cancer, rectum cancer, skin cancer, uterus cancer and the like can be utilized. Anti-pathogenic protein-antibodies may also be used. As the nucleic acids, nucleic acids which can be used as probes for certain genes or pathogenic genes may be used.

When antibodies or nucleic acids such as those mentioned above are used as the detection system, the detection system contained in the diagnostic marker of the present invention specifically binds to cancerous antigens or oncogenes, and as a result, lesions such as cancer cells and cancer tissues are immunologically stained with the diagnostic marker of the present invention. The lesions that emit fluorescence can be recognized under irradiation with near infrared rays or far infrared rays using an infrared laser or other.

Another embodiment of the diagnostic marker of the present invention relates to those comprising a substance for amplification system, e.g., avidin or biotin, as the detection system that is introduced with the fluorescent functional group. For example, where a conventionally and commonly used biotin-labeled anti-cancer antigen-antibody is applied to a living body, labeling can be carried out by coupling an anti-cancer antigen-antibody with a biotin-labeled antibody. After such labeling is completed, the diagnostic marker of the present invention containing avidin as the detection system is coupled to the biotin-labeled antibody, thereby the labeling with the biotin-labeled antibody can be amplified by the diagnostic marker of the present invention, and early cancers can be detected by means of an infrared laser or the like. Any substances for amplification system may be used so far that they can amplify labelings as mentioned above.

In addition, the aforementioned substances for amplification system can be bound to antibodies or nucleic acids such as those mentioned above, and then the products can be used as the detection system for the diagnostic marker of the present invention. For example, an antibody obtained by binding an anti-cancer antigen-antibody with avidin can be used as the detection system of the diagnostic marker of the present invention. Alternatively, a secondary antibody can also be used as the detection system of the diagnostic marker of the present invention. The above-explained detection systems are given merely as examples, and accordingly, the detection systems which can be used for the diagnostic marker of the present invention are not limited to those mentioned above. Any detection system may be used so far that they have properties of substantially specific binding to target cells or target tissues as objects of examination and diagnosis.

The diagnostic marker of the present invention are not limited to those in which the fluorescent functional group and the detection system as mentioned above are bound to each other directly or by means of a linker. For example, the fluorescent functional group and the detection system can be bound by means of a protein such as albumin, which are obtained by introducing the fluorescent functional group and the detection system into a protein such as albumin. A protein, e.g., albumin, can be introduced with one or more, preferably about 10 or more of the aforementioned fluorescent functional groups, and can easily be introduced with the detection system such as an antibody. Accordingly, diagnostic markers utilizing protein as mentioned above are preferred embodiments of the present invention.

The diagnostic marker according to a further embodiment of the present invention comprises the detection system bound with a fluorescent functional group which emits fluorescence having a wavelength of 780 nm or more, preferably 780–840 nm or more when irradiated with excitation light having a wavelength of 600–800 nm. As the fluorescent functional groups as mentioned above, any groups may be used so far that they emit fluorescence having a wavelength of 780 nm or more when irradiated with excitation light having a wavelength of 600–800 nm, as well as those derived from the groups of the formulas (I) and (II). Compounds for introducing such fluorescent functional groups can be appropriately chosen by those skilled in the art depending on the purpose of use of the diagnostic marker, sort of excitation light used and the like.

For example, compounds having near infrared ray-absorption property such as cyanin type compounds, phthalocyanine type compounds, dithiol nickel complexes type compounds, naphthoquinone-anthraquinone type compounds, indophenol type compounds, azo type compounds may be used to bind the fluorescent functional group to the detection system. Where these compounds are bound to the detection system directly or by means of a linker, their absorption wavelength may sometimes shift to longer wavelengths. Therefore, the wavelengths of the excitation light for the compounds used for introducing the fluorescent functional groups may be lower than 600 nm. These usable compounds may preferably have the groups represented by "Z" defined in the above general formulas (III) and (V) to facilitate the introduction of the fluorescent functional group into the detection system. Where these groups are not involved, the fluorescent functional group and the detection system are bound to each other by means of a linker available to those skilled in the art.

The diagnostic agent provided by the present invention is characterized in that it contains the aforementioned diagnostic marker as an active ingredient. The diagnostic agent of the present invention is advantageous since it can be excited with near infrared rays or far infrared rays, and causes no damage on living tissues or DNAs when used for a diagnosis. In addition, the diagnostic agent of the present invention has characteristic feature of extremely high water solubility. Among the diagnostic agent of the present invention, diagnostic agents comprising diagnostic markers that emit fluorescence having a longer wavelength than about 820 nm when irradiated with excitation light of 780 nm are particularly preferred. The diagnostic agent of the present invention may contain one or more of the diagnostic markers.

The diagnostic agents of the present invention may be provided in the form of solutions obtained by dissolving the aforementioned diagnostic markers in aqueous mediums such as various kinds of buffers, preferably physiological saline or buffers such as phosphate buffer, or solid preparations in the form of powders as fine particles or lyophilized powders which can be dissolved by adding physiological saline or buffers such as phosphate buffer at the time of diagnoses or clinical tests. However, the forms of the diagnostic agent are not limited to those mentioned above, and forms may suitably be chosen by those skilled in the art depending on the purpose of use and other.

As pharmacologically and pharmaceutically acceptable additives for the manufacture of the diagnostic agent of the present invention, for example, excipients, disintegrators and disintegrating aids, binders, lubricants, coating agents, coloring materials, diluents, base materials, solubilizers or dissolving aids, isotonicities, pH modifiers, stabilizers, propellants, thickeners and the like may be used. For example, excipients such as glucose, lactose, D-mannitol, starch, or crystalline cellulose; disintegrators or disintegrating aids such as carboxymethylcellulose, starch, or carboxymethylcellulose calcium; base materials such as vaseline, liquid paraffin, polyethylene glycol, gelatin, china clay, glycerin, purified water, or hard fat; isotonicities such as glucose, sodium chloride, D-mannitol, or glycerin; pH modifiers such as inorganic acids, organic acids, inorganic bases, or organic bases; pharmaceutically active substances that increase stability such as vitamin A, vitamin E, or coenzyme Q may be added.

A method for utilizing the diagnostic agent containing the diagnostic marker of the present invention will be explained, for example, as for an examination process using an infrared ray endoscope. A focal portion that emit fluorescence can be detected by staining a lesional portion with endoscopic splay or application of the aforementioned diagnostic agent, having a concentration of about 0.1 to 1,000 mg/ml, onto a suspected tissue containing the focal portion; appropriately washing the tissue to remove excess diagnostic agent therefrom; and then irradiating the tissue with near infrared rays or far infrared rays, more specifically, laser excitation light having a wavelength of, for example, 600–800 nm, preferably around 780 nm. Although the diagnostic markers of the present invention are characterized in that they can be directly applied to living bodies, it should be understood that the methods of using the diagnostic markers of the present invention are not limited to those applied to living bodies, and that the methods are also applicable to fixed specimens such as paraffin embedded preparations.

The detection of fluorescence can be carried out, for example, by means of infrared ray endoscope, infrared ray microscope and the like. For example, filters having given transmission properties may be used in combination, whose specific example includes a combination comprises a filter having shielding property against the excitation light together with one or more filters for detecting fluorescence. Where endoscopic examination is carried out by applying the diagnostic marker of the present invention to a living body, an endoscope having a magnification of about 10 to 1,000 may be used, and for example, an infrared ray endoscope having a microscopic level of magnification may preferably be used. The endoscope may preferably be provided with means for spraying or applying the diagnostic agent of the present invention and means for washing.

Where the diagnostic markers of the present invention is applied to tissues or specimens removed from living bodies, an infrared ray microscope can be used for the detection of fluorescence. It is also possible to recognize stained portions by observation of preparations under normal light, and then carry out image analysis by using a computer after taking photographs with an infrared film in a darkroom under infrared rays, or alternatively, recording in videotapes.

EXAMPLES

The present invention will be further explained more specifically by referring to the following examples. However, the scope of the present invention is not limited to the following examples.

Example 1

Preparation of the Labeling Compounds

Compound of the formula (III) were prepared as labeling compounds for the manufacture of the diagnostic markers of the present invention according to the following scheme. The compound numbers mentioned in the following example correspond to those shown in the schemes.

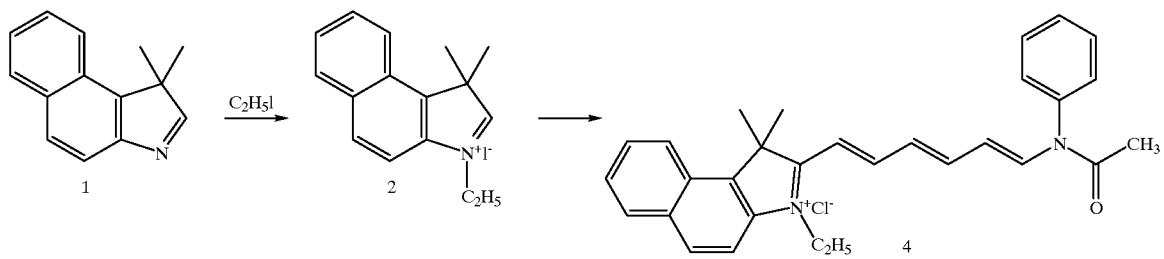

-continued
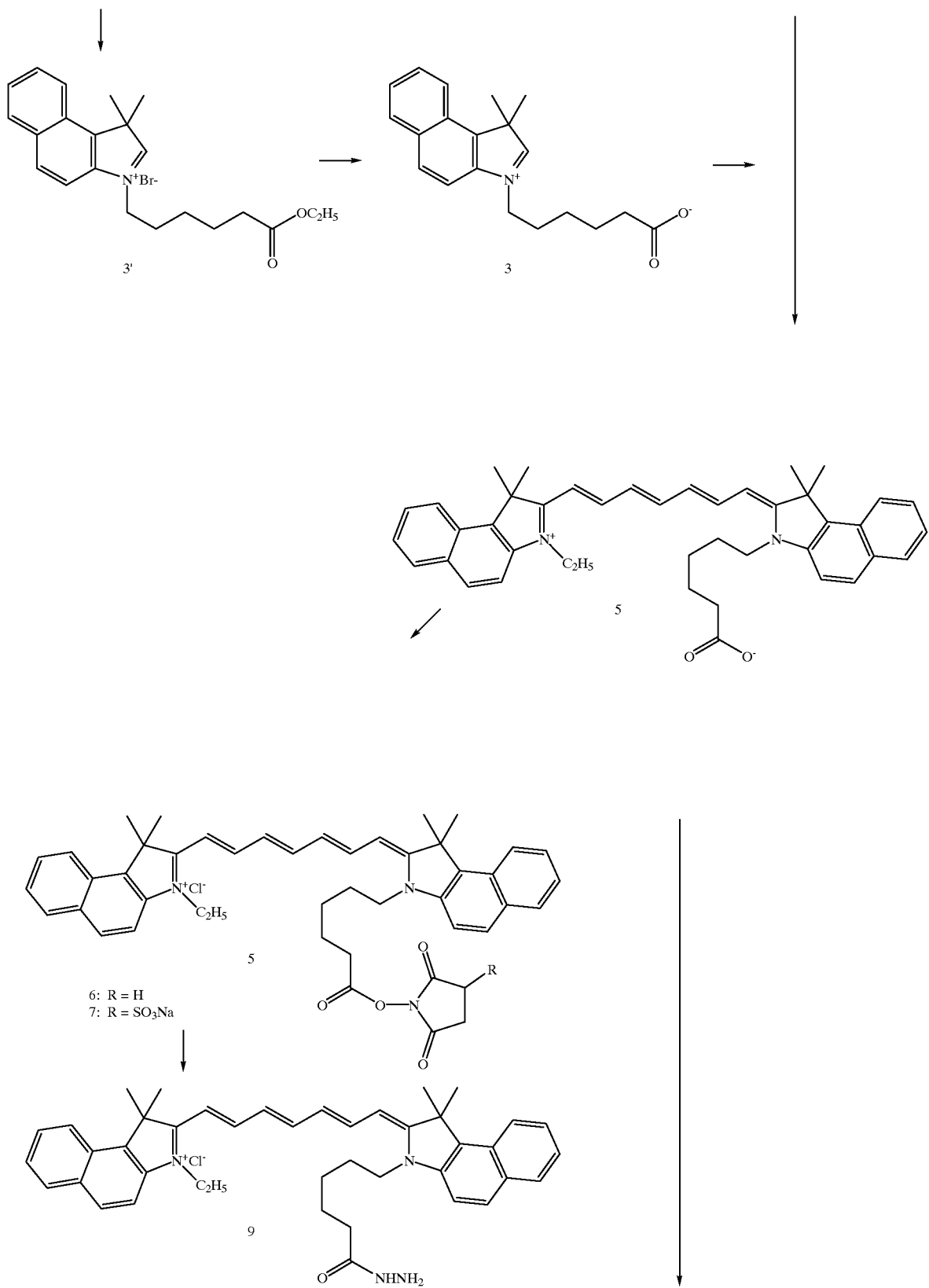

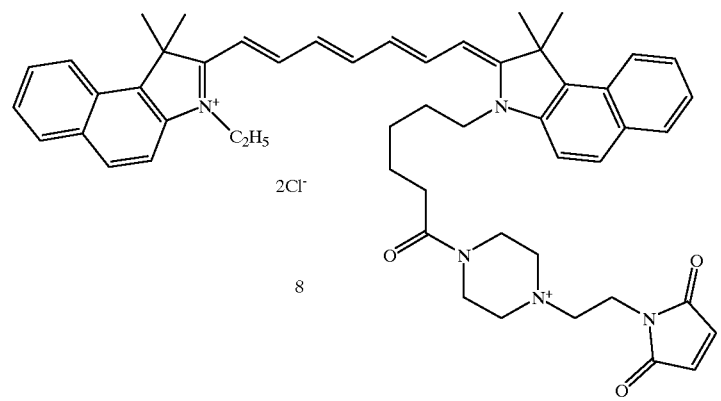
8
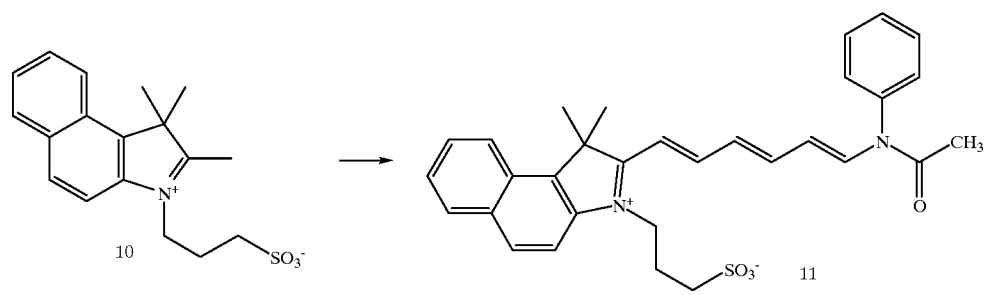
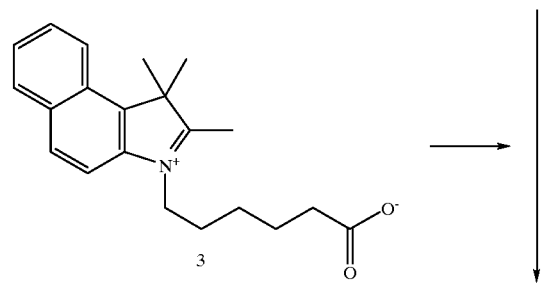
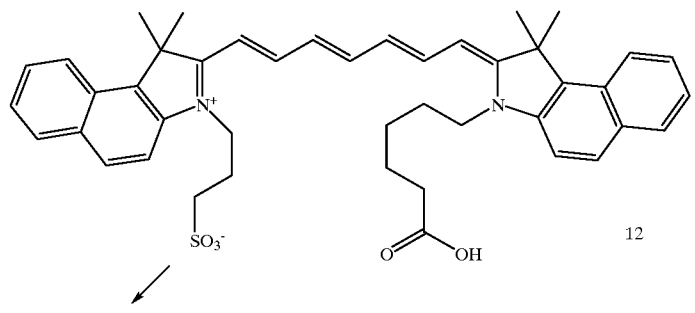

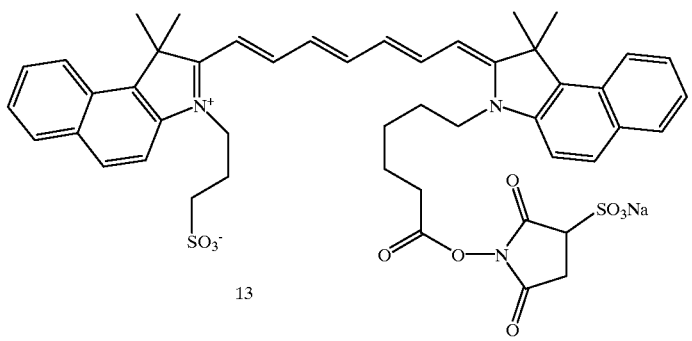

13

Compound 1 (5 g, 23.9 mmol, obtained from Daiichi Pure Chemicals Co., Ltd.) in acetonitrile (100 ml) was added with iodoethane (2.84 ml, 35.5 mmol) and refluxed for five hours. The reaction mixture was concentrated under reduced pressure, and the residue was added with ether (200 ml) to form crystals. The resulting crystals were filtered and washed with ether, and then dried under reduced pressure to obtain Compound 2 as pale reddish brown powder (6.83 g, yield 78.2%).

Compound 1 (5 g, 23.9 mmol) in DMF (100 ml) was added with ethyl 6-bromocaproate (6.32 ml, 35.5 mmol) and the mixture was heated at 80° C. for 16 hours. The reaction mixture was concentrated under reduced pressure and ether (200 ml) was added to the residue for crystallization. The resulting crystals were filtered and washed with ether, and then dried under reduced pressure. The crystals were added with a mixed solution of 1M aqueous solution of sodium hydroxide and methanol (1/1, 30 ml) and the mixture was stirred at room temperature for two hours. Methanol was evaporated under reduced pressure, and the aqueous solution was neutralized with 4M aqueous hydrochloric acid and washed three times with chloroform. The aqueous solution was concentrated under reduced pressure to obtain Compound 3 as red solid (5.75 g, yield 74.4%).

Compound 2 (5 g, 13.7 mmol) and glutaconaldehyde dianil hydrochloride (3.90 g, 13.7 mmol) were suspended in acetic anhydride (50 ml) and then the mixture was heated at 100° C. for 1.5 hours. The red solution was poured into water (300 ml) and the deposited dark red solid was collected by filtration. The product was washed with water and dried under reduced pressure to obtain Compound 4 as dark red powder(6.02 g, yield 101%).

Compound 4 (220 mg, 0.505 mmol) and Compound 3 (164 mg, 0.507 mmol) were dissolved in pyridine (3 ml) and the mixture was stirred at 50° C. for one hour. The reaction mixture was concentrated under reduced pressure, and the residue was purified using a silica gel column chromatography (eluent: 1–20% methanol-chloroform) to obtain Compound 5 as black green solid (49 mg, yield 15.5%).

Compound 5 (40 mg, 64 μmol) in DMF (1 ml) was added with N-hydroxysuccinic anhydride (8.8 mg, 76 μmol) and N,N'-dicyclohexylcarbodiimide (DCC, 26.4 mg, 0.128 mmol) and the mixture was allowed to react at 4° C. overnight. Ether (10 ml) was added to the reaction mixture and the resulting residue was washed three times with ether. The solid mass was dissolved in chloroform (400 μl), and the solution was added with 0.1M aqueous hydrochloric acid (200 μl) and stirred. Then, the chloroform layer was separated and washed three times with water. The chloroform solution was concentrated under reduced pressure to obtain Compound 6 as black green solid (a labeling compound of the formula (III)) (38 mg, yield 78.5%). MS (FAB) m/e= 720(M$^+$); Fluorescence spectra: $\lambda_{ex}$=769 nm, $\lambda_{em}$=820 nm (10% DMSO in water).

Compound 5 (20 mg, 32 μmol) in DMF (1 ml) was added with sodium N-hydroxysuccinic anhydride sulfonate (8.3 mg, 38 μmol) and N,N'-dicyclohexylcarbodiimide (13.2 mg, 64 μmol), and the mixture was allowed to react at 4° C. overnight and then filtered. Ether (10 ml) was added to the filtrate and the resulting residue was washed three times with ether. The solid mass was dissolved in DMF (400 μl), and the solution was added with 0.1M aqueous hydrochloric acid (200 μl) and stirred. Then, the chloroform layer was separated and washed three times with water. The chloroform solution was concentrated under reduced pressure to obtain Compound 7 as black green solid (labeling compound of the formula (III), 17 mg, yield 66.4%). MS (FAB) m/e=822 (M$^+$Na); Fluorescence spectra $\lambda_{ex}$=769 nm, $\lambda_{em}$=820 nm (10% DMSO in water).

Compound 5 (20 mg, 32 μmol) in DMF (0.5 ml) was added with N-(2-(N'-maleimide)ethyl)piperazine dihydrochloride (PEM, 4.4 mg, 38 μmol), triethylamine (TEA, 20 μl, 0.146 mmol) and DCC (10.2 mg, 49 μmol), and the mixture was allowed to react at 4° C. overnight. Ether (10 ml) was added to the reaction mixture and the resulting residue was washed three times with ether. The solid mass was dissolved in chloroform (400 μl), and the solution was added with 0.1M aqueous hydrochloric acid (200 μl) and stirred. Then, the chloroform layer was separated and washed three times with water. The chloroform solution was concentrated under reduced pressure to obtain Compound 8 as black green solid (labeling compound of the formula (III), 20 mg, yield 70.5%). MS (FAB) m/e=814(M$^+$); Fluorescence spectra $\lambda_{ex}$=773 nm, $\lambda_{em}$=821 nm (10% DMSO in water).

Example 2

Preparation of the Labeling Compound

Compound 6 (20 mg, 26.4 μmol) in DMF (0.5 ml) was added with hydrazine monohydrochloride (9.0 mg, 0.131 mmol) and the mixture was allowed to react overnight. The reaction mixture was filtered and the filtrate was concentrated under reduced pressure. The residue was dissolved in chloroform (0.5 ml) and the chloroform solution was washed with water three times. The chloroform layer was concentrated under reduced pressure to obtain Compound 9 as black green solid (16 mg, yield 90.0%). MS (FAB) m/e=637(M$^+$); Fluorescence spectra: $\lambda_{ex}$=771 nm, $\lambda_{em}$=820 nm (10% DMSO in water).

Compound 10 (5.0 g, 15.1 mmol) and glutaconaldehyde dianil hydrochloride (4.40 g, 15.1 mmol) were suspended in a mixed solution of acetic anhydride (20 ml) and acetic acid (300 ml), and the mixture was heated at the refluxing temperature for five hours. The red solution was concentrated under reduced pressure and the resulting residue was added with a mixture of ethyl acetate and water (200 ml) to form a suspension, and then resulting black red solid was collected by filtration. The product was washed with water and dried under reduced pressure to obtain Compound 11 as black red powder (5.33 g, yield 65.2%).

Compound 11 (167 mg, 0.308 mmol) and Compound 3 (100 mg, 0.309 mmol) were dissolved in pyridine (3 ml) and the solution was stirred at 50° C. for one hour. The reaction mixture was concentrated under reduced pressure. The resulting residue was dissolved in water (10 ml) and the solution was adjusted to pH 3, and then applied to Sephadex LH20 column for purification (eluent: water) to obtain Compound 12 as black green solid (51 mg, yield 23.1%).

Compound 12 (30 mg, 41.8 μmol) in a 50 v/v % aqueous solution of THF (1 ml) was added with sodium N-hydroxysuccinic anhydride-sulfonate (16.8 mg, 77.4 μmol) and N,N'-dicyclohexylcarbodiimide (25.8 mg, 0.125 mmol), and the mixture was allowed to react at 4° C. overnight and then filtered. The filtrate was concentrated under reduced pressure at a temperature of 20° C. or less. The residue was added with ethyl acetate (10 ml) and the deposited crystals were further washed with ether three times. These crystals were dissolved in water (200 μl) and purified using a Sephadex LH20 column (eluent: water) to obtain Compound 13 as black green solid (labeling compound of the formula (III), 34 mg, yield 88.8%). MS (FAB) m/e=892(M⁻); Fluorescence spectrum $\lambda_{ex}$=771 nm, $\lambda_{em}$=822 nm (water).

Example 3

Preparation of the Labeling Compound

Labeling compounds of formula (V) used for the manufacture of the diagnostic markers of the present invention were prepared according to the following scheme. The compound numbers mentioned in the following example correspond to those shown in the schemes.

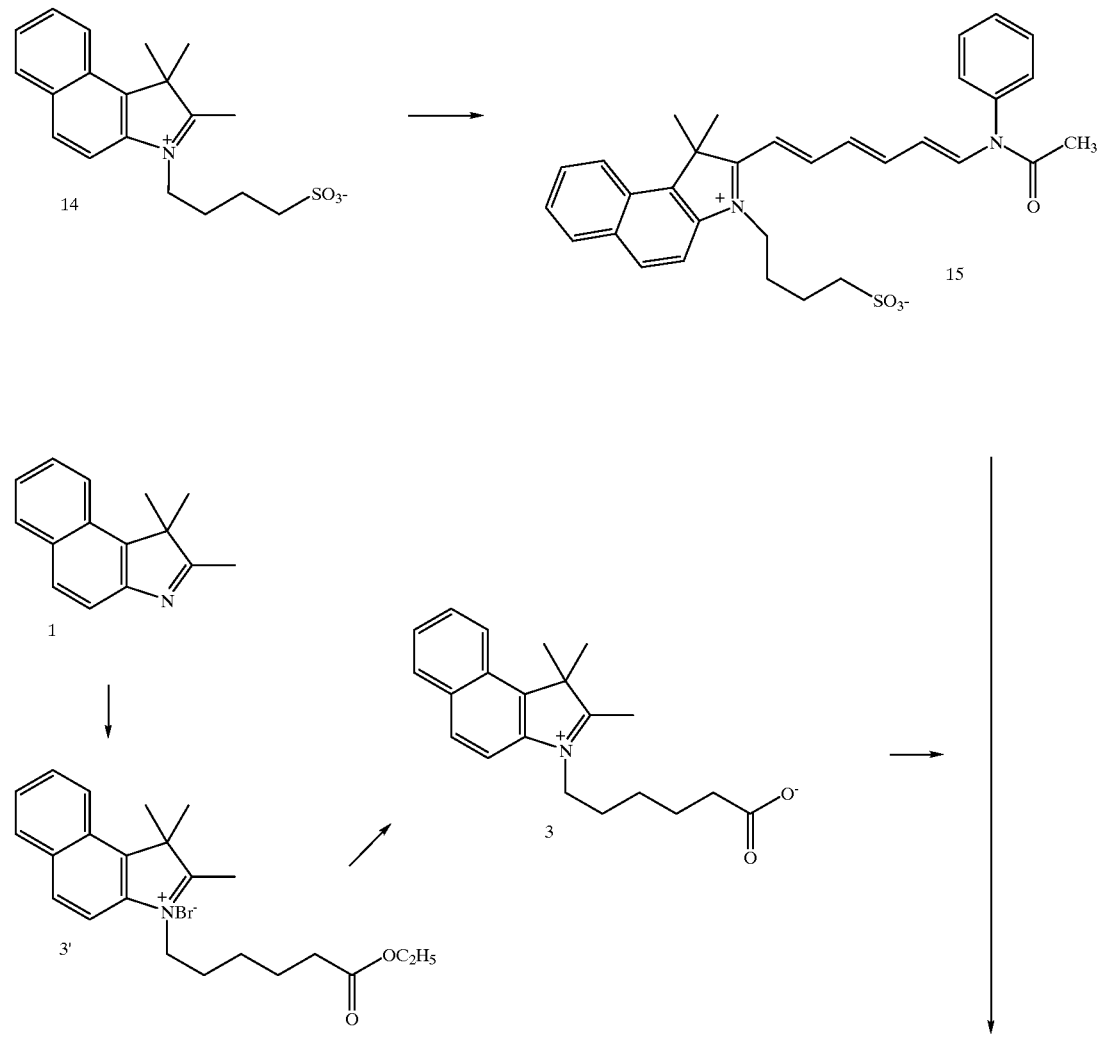

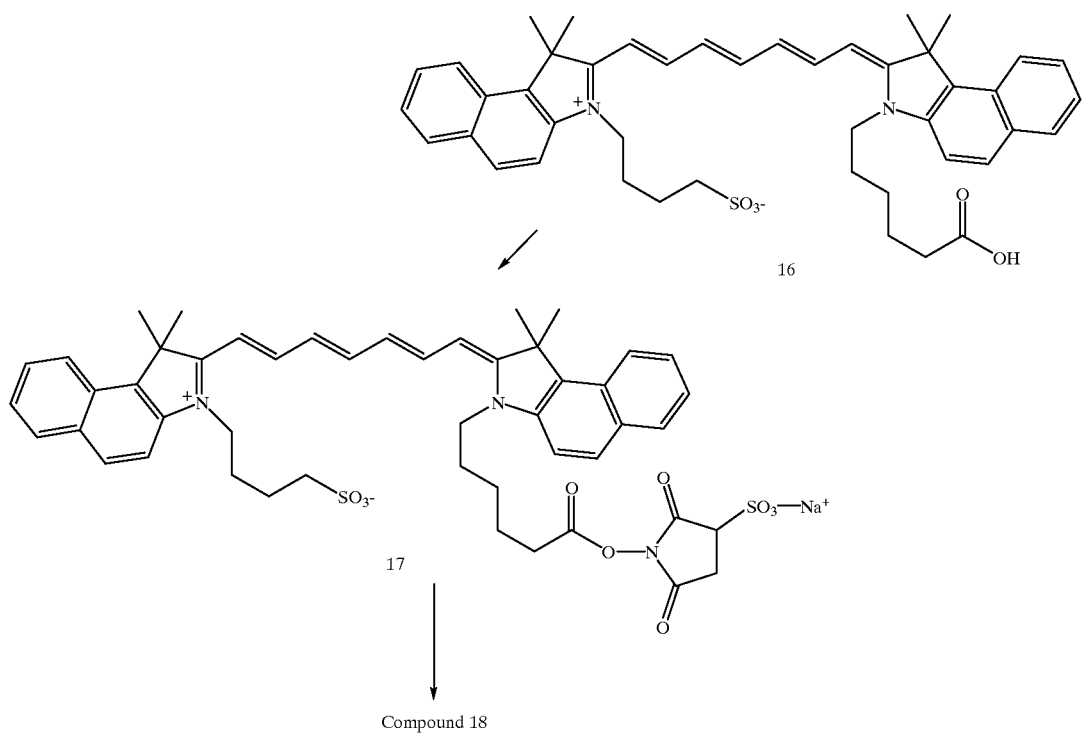

Compound 18

Compound 14 (5.0 g, 14.5 mmol) and glutaconaldehyde dianil hydrochloride (4.23 g, 14.5 mmol) were suspended in a mixed solution of acetic anhydride (20 ml) and acetic acid (300 ml) and the mixture was heated at the refluxing temperature for five hours. The resulting red solution was concentrated under reduce pressure and the resulting residue was added with a mixture of ethyl acetate and water (200 ml) to form a suspension, and then black red solid was collected by filtration. The product was washed with water and dried under reduced pressure to obtain Compound 15 as black red powder (5.20 g, yield 66.1%).

Compound 15 (300 mg, 0.553 mmol) and Compound 3 (179 mg, 0.553 mmol) were dissolved in pyridine (5 ml) and the mixture was stirred at 50° C. for one hour. The reaction mixture was concentrated under reduced pressure. The resulting residue was dissolved in water (10 ml), and the solution was adjusted to pH 3 and then applied to a Sephadex LH20 column for purification (eluent: methanol) to obtain Compound 16 as black green solid (105 mg, yield 25.9%).

Compound 16 (106 mg, 0.145 mmol) in 50 v/v % aqueous solution of THF (3 ml) was added with sodium N-hydroxysuccinic anhydride-sulfonate (65.2 mg, 0.287 mmol) and N,N'-dicyclohexylcarbodiimide (129 mg, 0.596 mmol), and the mixture was allowed to react at 4° C. overnight and then filtered. The filtrate was concentrated under reduced pressure at a temperature of 20° C. or less. The residue was added with ethyl acetate (10 ml) and the deposited crystals were further washed with ether three times to obtain Compound 17 as black green solid (110 mg, yield 80.7%). MS (FAB) m/e=906 (M⁻); Fluorescence spectra: $\lambda_{ex}$=768 nm, $\lambda_{em}$=807 nm (water).

The above-obtained Compound 17 (100 mg, 0.11 mmol) was dissolved in methanol (2 ml) and the solution was added with a solution of sodium iodide (1 g, 6.7 mmol) in methanol (5 ml). The methanol solution was concentrated to a half of the volume and cooled to 4° C. overnight. The precipitated crystals were collected by filtration. The obtained green crystals were dried in a vacuum desiccator to give Compound 18 (labeling compound of the formula (V), 85 mg, yield 72%). Data of water-solubility and infrared absorption spectrum data (IR) were obtained before the formation of the salt with sodium iodide (zwitterion type) and after the salt formation. The iodide content was determined by the Schöniger method.

Figure 1B:
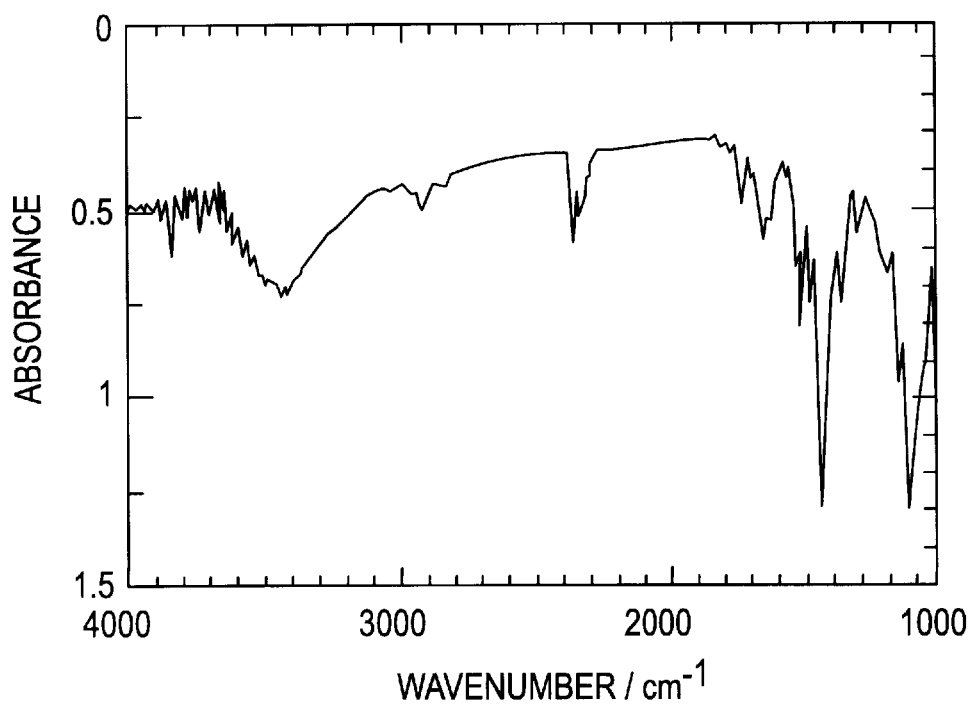

Changes in the infrared absorption spectrums were recognized between Compound 18 that accepted sodium iodide to form the salt and indocyanine green N-hexanoic acid sulfosuccinimide ester in the form of zwitterion use as the starting material (Compound 17), i.e., absorptions at 2360 and 1740 cm⁻¹ observed in Compound 17 as the zwitterion disappeared in Compound 18 (see, FIG. 1: (a) shows the spectrum of Compound 18 and (b) shows that of Compound 17, i.e., the compound before the salt formation). From these results, it is apparent that the compound that forms an intramolecular zwitterion and the compound that forms the double salt with sodium iodide have distinguishable crystalline structures.

Example 4

Preparation of the Labeling Compound

Indocyanine green-N-butanoic acid sulfosuccinimide ester (Compound 19) was prepared according to the method of Example 3. Compound 19 (150 mg, 0.17 mmol) was dissolved in methanol (3 ml) and the solution was added with a solution of sodium iodide (1.5 g, 10 mmol) in methanol (8 ml). The methanol was concentrated to a half of the volume and the concentrate was cooled to 4° C. overnight. The precipitated crystals were collected by filtration.

The obtained green crystals were dried in a vacuum desiccator to give Compound 20 (labeling compound of the formula (V), 117 mg, yield 66%). Data of water-solubility and infrared absorption spectra data (IR) were obtained before and after the salt formation with sodium iodide. Iodine content was determined by the Schöniger method.

Example 5

Preparation of the Labeling Compound

Indocyanine green-N-hexanoic acid sulfosuccinimide ester (Compound 21) was prepared according to the method of Example 3. Compound 21 (100 mg, 0.11 mmol) was dissolved in methanol (2 ml) and the solution was added with a solution of sodium perchlorate (0.3 g, 2.5 mmol) in methanol (20 ml). The methanol was concentrated to a quarter of the volume under reduced pressure and the concentrate was cooled to 4° C. overnight. The precipitated crystals were collected by filtration. The obtained green crystals were dried in a vacuum desiccator to give Compound 22 (labeling compound of the formula (V), 23 mg, yield 21%). Data of water-solubility and IR were obtained before and after the salt formation with sodium perchlorate.

TABLE 1

| Labeling compound | Zwitterion type | Double salt type |
|---|---|---|
| Example 3 | Compound 17 | Compound 18 |
| Water solubility | 1 mg/10 ml or more | 1 mg/0.8 ml |
| IR (cm$^{-1}$) | 2360, 1740 | Absorptions in the left column disappeared |
| Iodide content | — | 12.3% |
| Example 4 | Compound 19 | Compound 20 |
| Water solubility | 1 mg/10 ml or more | 1 mg/0.9 ml |
| IR (cm$^{-1}$) | 2370, 1790 | Absorptions in the left column disappeared |
| Iodide content | — | 13.5% |
| Example 5 | Compound 21 | Compound 22 |
| Water solubility | 1 mg/10 ml or more | 1 mg/5 ml |
| IR (cm$^{-1}$) | 2370, 1790 | Absorptions in the left column disappeared |

Compound 18

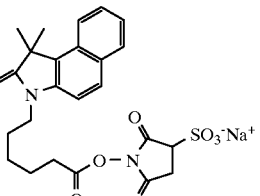

Compound 20

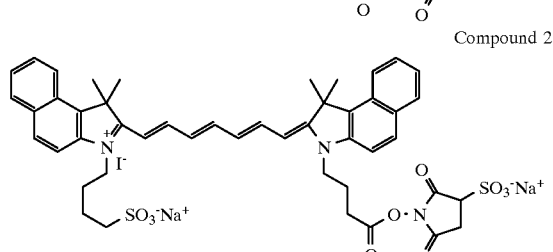

Compound 22

TABLE 1-continued

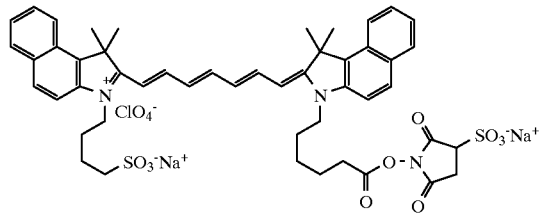

Example 6

Preparation of the Labeling Compound

Compound 23 was obtained by treating Compound 13 with the methanol solution of sodium iodide according to the method of Example 2. The infrared absorption spectrum of Compound 13 used as the starting material was compared with that of Compound 23 as the labeling compound, the absorptions at 2360 and 1740 cm$^{-1}$ observed in Compound 13 were not observed for Compound 23.

Example 7

Preparation of the Diagnostic Marker (a) Purification of Antibody

From a culture supernatant (M613, Dabko) containing anti-EMA (Epitherial Membrane Antigen) antibodies, Anti-EMA monoclonal antibodies were purified using MabTrap GII (Pharmacia) as follows. The culture supernatant (4 ml) was added with a binding buffer (4 ml) and then applied to a MabTrap GII column equilibrated with the binding buffer beforehand. After washing with the binding buffer (5 ml), elution buffer (3 ml) was applied and effluent buffer was collected as 0.5 ml fractions. Fractions were measured using a spectrophotometer and those having an absorbance of 0.05 or more at 280 nm were collected as a purified IgG fraction, and then the buffer was changed to 0.1M phosphate buffer (pH 7.5) using a PD-10 column (Pharmacia) and purification degree was measured with SDS-PAGE (Daiichi Pure Chemicals). From 4 ml of the culture supernatant, 725 μg of purified anti-EMA monoclonal antibodies were obtained.

(b) Binding of the Labeling Compound to Antibody

Figure 2:
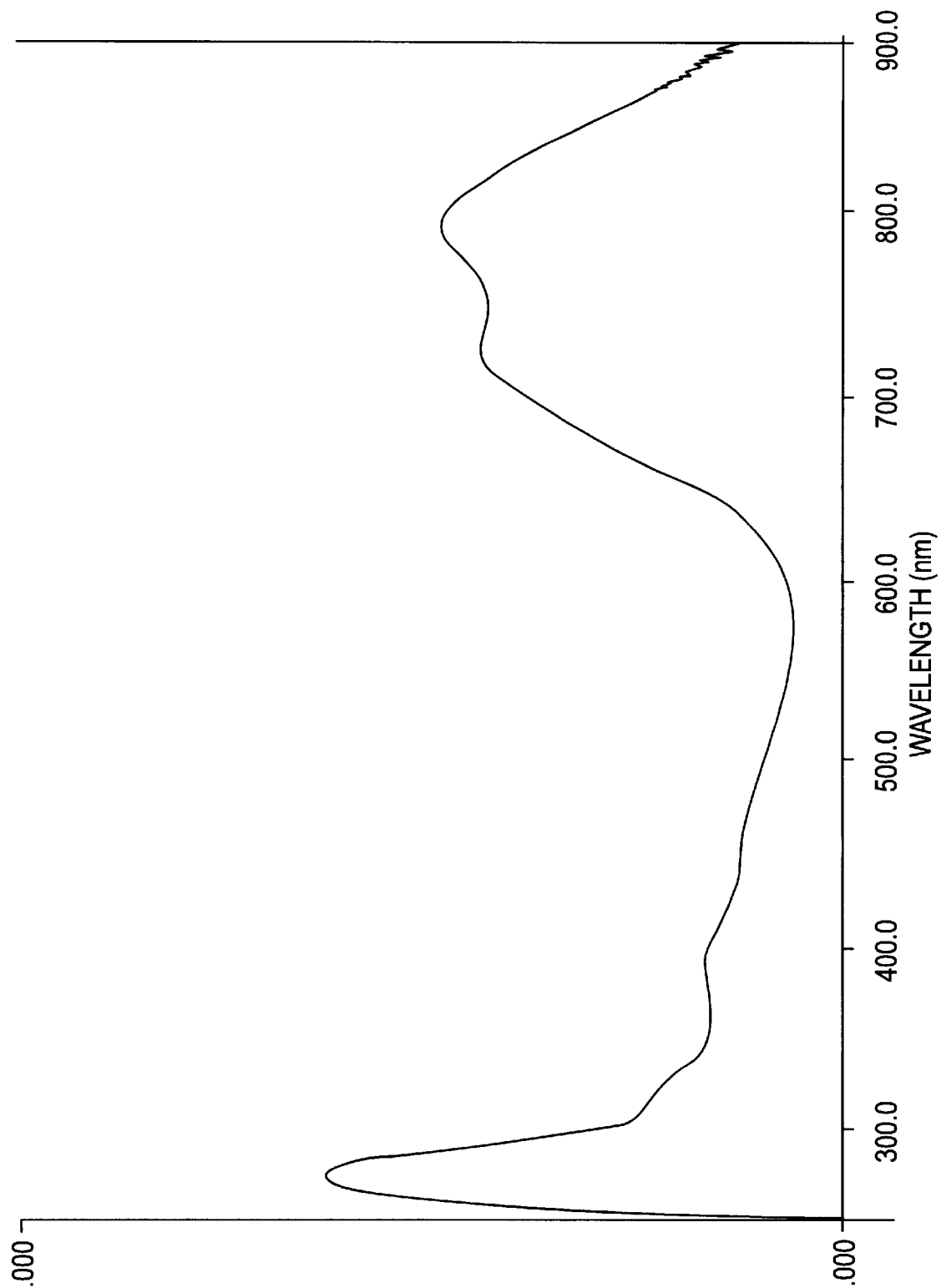
FIG. 2 shows au ultraviolet and visible absorption spectrum of a diagnostic marker of the present invention (74 μg/ml) which was obtained by binding Compound 6 as a labeling compound to an anti-EMA antibody.

A solution of ICG-OSu (Compound 6) in DMF (0.125 ml, 0.8 mg/ml) was added to 100 mM phosphate buffer (0.5 ml) containing the above purified antibodies (500 μg) and the mixture was left stand at 30° C. for 30 minutes. The reaction mixture was applied to a PD-10 column equilibrated beforehand with the same reaction buffer to separate unreacted ICG-OSu. The buffer of the protein fractions was changed to 0.1M phosphate buffer/0.05% sodium azide (pH 7.4) using a PD-10 column to obtain 74 μg protein/ml of the diagnostic marker of the present invention in which the anti-EMA antibodies bound to the labeling compound (Compound 6). After then, 0.1% BSA was further added for storage. The ultraviolet and visible absorption spectrum of the diagnostic marker is shown in FIG. 2.

The conditions for measuring the above spectrum were as follows: measuring apparatus: Hitachi U-3200 spectrophotometer; measuring medium: 100 mM phosphate buffer (pH 7.4), 0.05% sodium azide; and scanning speed: 300.0 nm/min. After then, 0.1% BSA was added for storage. The number of antibodies bound to the labeling compound was 12 mol labeling compound/mol antibody when determined by the antibody concentration measured by BCA protein assay reagent (Pierce) and the molar absorption coefficient of the labeling compound measured in DMSO.

Example 8

Preparation of the Diagnostic Marker

Figure 3:
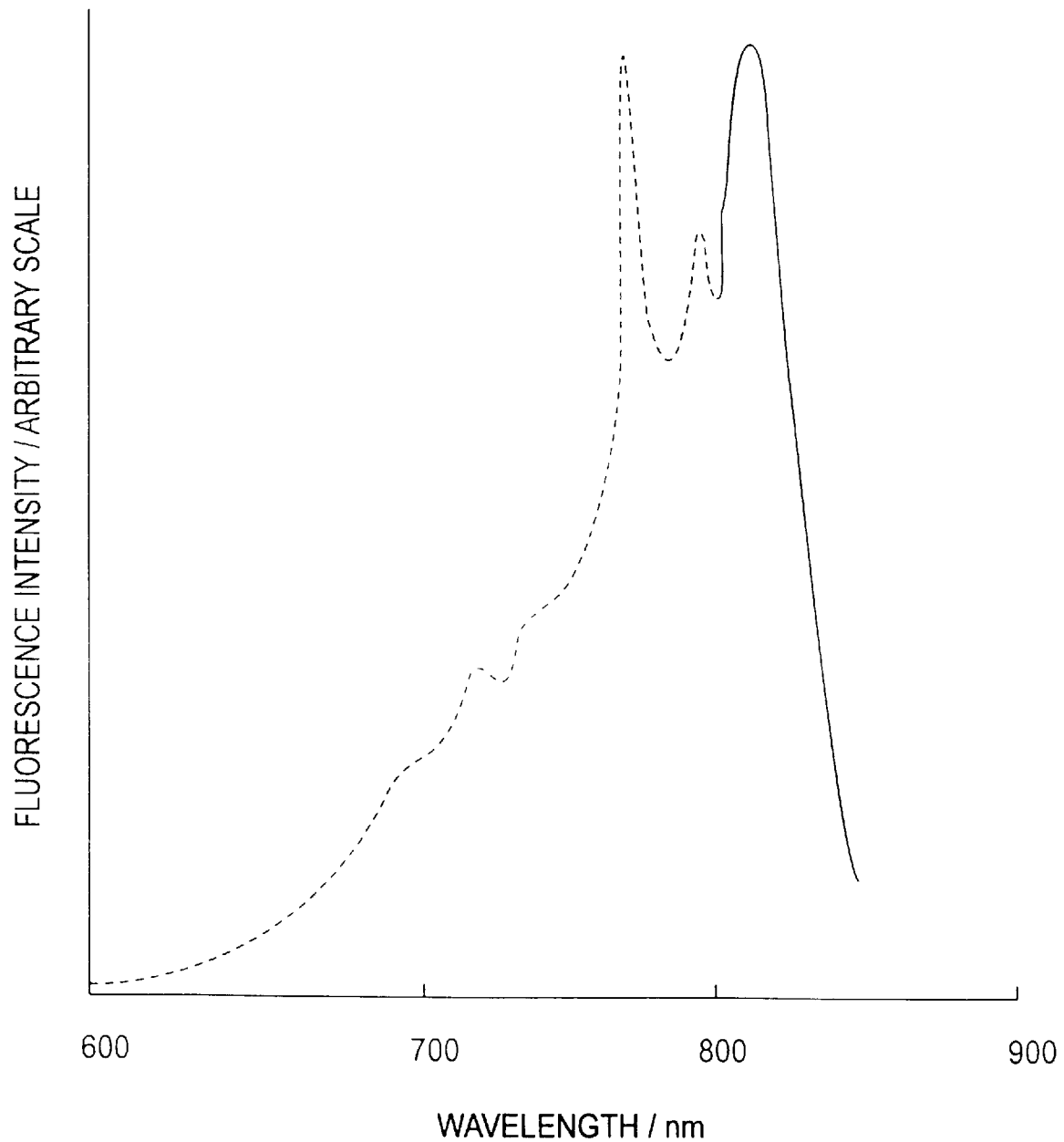
FIG. 3 shows a fluorescent spectrum of a diagnostic marker of the present invention obtained by binding Compound 18 as a labeling compound to a human IgG. In the figure, the solid line represents an emission spectrum and the broken line represents an excitation spectrum.

Compound 18 (1 mg) was dissolved in water (0.94 ml) so as to obtain a 1 mM solution. Human IgG (1 mg) was dissolved in 50 mM sodium carbonate buffer (1 ml, pH 8.5) and the solution was added with the above solution containing Compound 18 (0.2 ml) and then the mixture was allowed to react at 30° C. for one hour. The reaction mixture was applied to a Sephadex G-25 column to separate the diagnostic marker of the present invention. As the buffer for separation, 50 mM phosphate buffer (pH 7.4) was used. Unreacted Compound 18 was remained at the upper end of the Sephadex gel, and consequently the diagnostic marker was successfully separated therefrom. The resulting diagnostic marker was lyophilized and refrigerated at −20° C. for storage. One mg of the diagnostic marker was dissolved in 100 ml of 50 mM phosphate buffer (pH 7.4) and fluorescence spectrum was measured. The results are shown in FIG. 3.

Example 9

Preparation of the Diagnostic Marker

A solution of Compound 18 in DMF (0.125 ml, 0.8 mg/ml) was added to 100 mM phosphate buffer (0.5 ml) containing the purified antibodies obtained in Example 7 (500 µg) and the mixture was left stand at 30° C. for 30 minutes. This reaction mixture was applied to a PD-10 column equilibrated with the same reaction buffer beforehand to separate unreacted Compound 18. The buffer of the protein fractions was changed to 0.1M phosphate buffer/0.05% sodium azide (pH 7.4) using a PD-10 column to obtain 74 µg protein/ml of a diagnostic marker of the present invention in which Compound 18 bound to the anti-EMA antibody. After then, 0.1% BSA was added for storage.

Example 10

Binding of the Labeling Compound to a Protein

A BSA solution was prepared by dissolving BSA (10 mg, 0.151 µmol, Wako Pure Chemical Industries) in HEPES buffer (3.0 ml). The labeling compound (Compound 6, 2.0 mg, 2.64 µmol) was dissolved in DMSO (150 µl), and the solution was mixed with the BSA solution mentioned above, and then the mixture was left in refrigerator overnight. Gel filtration was performed using a PD-10 column in the same manner as described above to obtain the marker protein in which BSA was introduced with fluorescent functional groups derived from the labeling compound. Because green solution derived from the labeling compound was not retained in the column during the gel filtration after the completion of the reaction, it can be considered that all of the labeling compounds reacted with BSA and about 17.5 fluorescent functional groups were introduced per one molecule of BSA.

Example 11

Preparation of the Diagnostic Marker (a) A solution of Compound 6 in DMF (0.5 ml, 4.6 mg/ml) was added to 100 mM phosphate buffer (pH 7.5, 5 ml) containing BSA (10 mg) and the mixture was left stand at 30° C. for 30 minutes. The reaction mixture was applied to a Sephadex G25 column equilibrated beforehand with the reaction buffer to separate the a complex (marker BSA) that was formed by the labeling compound and the protein from unreacted Compound 6. The buffer of the fractions containing the complex was changed to 20 mM phosphate buffer/0.15M NaCl (pH 7.0) by using a Sephadex G25 column to obtain about 8 mg of BSA that was introduced with fluorescent functional groups.

(b) Pepsin was added to the anti-CEA antibodies (1.0 mg/ml in 0.1M citric acid/0.15M NaCl, pH 4.0) so as to achieve 0.004 mg/ml of pepsin concentration, and then the mixture was allowed to react at 37° C. for two hours. The reaction mixture was added to TSKgel G3000SW equilibrated beforehand with 20 mM phosphate buffer, 0.15 M NaCl, and 1 mM EDTA to separate F(ab')2 from undigested IgG and digested fragments (about 500 µg). The F(ab')2 fractions were added with 2-aminoethanethiol hydrochloride so as to obtain a final concentration of 10 mM, and then the mixture was allowed to react at 37° C. for 90 minutes. The reaction mixture was applied to a Sephadex G25 column to remove 2-aminoethanethiol to give a solution containing Fab'.

(c) 50 µl of sulfo-SMCS solution (sulfo-EMCS, Dojindo Laboratories, 1 mg/ml, PBS) was added dropwise to a solution of the marker BSA (2 mg, 20 mM phosphate buffer/0.15 M NaCl, pH 7.0; PBS) with stirring, and the mixture was allowed to react for 20 minutes at room temperature. The reaction mixture was applied to a Sephadex G25 column equilibrated beforehand with PBS to separate the marker BSA activated with the sulfo-SMCS. The solution was added to the Fab' solution obtained in the above (b) and the mixture was allowed to react at room temperature for two hours with stirring. After the reaction completed, the reaction mixture was separated and purified by gel filtration using TSKgel G3000SW to obtain BSA that was introduced with the fluorescent functional groups and Fab'.

Example 12

Immunohistochemical Staining using Diagnostic Marker

The diagnostic marker of Example 6 was used as the diagnostic marker of the present invention. Paraffin section of the esophagal mucosa (about 10×10 mm; thickness, 2.5 µm) that had been revealed positive stainability with anti-EMA antibodies and non-fixed isolated sections of esophagus cancer were treated with the diagnostic marker, and colors were developed by the ABC method (avidin/biotin complex method) and degrees of the staining were observed by means of a microscope or an ordinary endoscope. In addition, preparations that were subjected to color development as described above were observed by means of an infrared ray endoscope to identify the stained portions, and the results were compared with the stained portions identified by the observation using an ordinary endoscope. The diagnostic markers with serial two-fold diluted concentrations were subjected to observations with an ordinary endoscope or an infrared ray endoscope, and their distinguishing properties were compared.

Excellent color developments were microscopically observed when 5-fold dilutions and 10-fold dilutions of the diagnostic marker were used, and stainabilities comparable to the anti-EMA antibodies as a control (50-fold dilution) were recognized. By the observation of the preparations using an ordinary endoscope, depositions of DAB (diaminobenzidine) was observed on the esophagal mucosa with the 10-fold dilution of the diagnostic marker, which were almost similar to and corresponding to the results obtained by the control.

Industrial Applicability

By using the diagnostic marker of the present invention, quasi-internal early diagnoses of epithelial neoplasm such as esophagus cancer, stomach cancer or large bowel cancer by means of an infrared endoscope, and identification and diagnosis of foci in surgical operations can be performed conveniently and accurately. Clinical tests and diagnoses utilizing the diagnostic marker of the present invention are free from damages on living tissues and DNAs due to ultraviolet excitation and can be performed directly to living organisms. Accordingly, they are useful as immuno-histochemical staining methods.

In addition, since the labeling compounds contained in the diagnostic marker of the present invention have characteristic features of extremely high water solubility, the diagnostic markers of the present invention are not absorbed in the gastrointestinal tract and advantageous to achieve highly safe clinical examination and diagnoses.

What is claimed is:

1. A diagnostic marker, comprising:

a detection system; and a fluorescent functional group that is bound to the detection system and represented by the following formula:

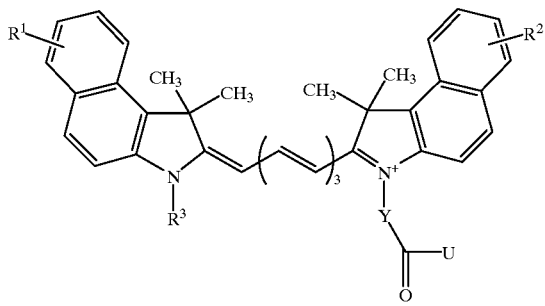

wherein $R^1$ and $R^2$ are independently selected from the group consisting of hydrogen, alkyl group, aryl group, alkoxy group, and sulfonic acid group; $R^3$ is selected from the group consisting of alkyl group, sulfonic acid-alkyl group, and amino-substituted alkyl group; Y is a $C_1$–$C_{10}$ alkylene group or a $C_1$–$C_{10}$ alkylene group containing at least one atom selected from the group consisting of oxygen, nitrogen, and sulfur; and U is a site at which the detection system binds.

2. The diagnostic marker of claim 1, wherein the fluorescent functional group directly binds to the detection system.

3. The diagnostic marker of claim 1, wherein the fluorescent functional group binds to the detection system through a linker.

4. The diagnostic marker of claim 3, wherein the linker comprises a protein.

5. The diagnostic marker of claim 1, wherein the detection system is selected from the group consisting of antibody, nucleic acid, and amplification system substance.

6. The diagnostic marker of claim 1, wherein the detection system comprises an anti-cancer antibody selected from the group consisting of antigen-antibody, antibacterial antibody, and antiviral antibody.

7. The diagnostic marker of claim 1, wherein the diagnostic marker emits fluorescence having a wavelength of at least 780 nm when irradiated with one of near and far infrared rays.

8. The diagnostic marker of claim 1, wherein the diagnostic marker comprises an active ingredient.

9. A method, comprising:

applying the diagnostic marker of claim 1 to living tissue; and performing an infrared endoscopic diagnosis on the living tissue.

10. The method of claim 9, wherein applying the diagnostic marker comprises immuno-histochemical staining.

11. A method, comprising:

applying the diagnostic marker of claim 1 to living tissue; and identifying a focus for a surgical operation in the living tissue.

12. The method of claim 11, wherein applying the diagnostic marker comprises immuno-histochemical staining.

13. A diagnostic marker, comprising:

a detection system; and a fluorescent functional group that is bound to the detection system and represented by the following formula:

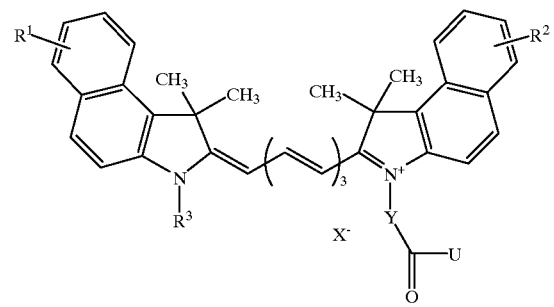

wherein $R^1$ and $R^2$ are independently selected from the group consisting of hydrogen, alkyl group, aryl group, alkoxy group, and sulfonic acid group; $R^3$ is selected from the group consisting of alkyl group, sulfonic acid-alkyl group, and amino-substituted alkyl group; $X^-$ is an anion; Y is a $C_1$–$C_{10}$ alkylene group or a $C_1$–$C_{10}$ alkylene group containing at least one atom selected from the group consisting of oxygen, nitrogen, and sulfur; and U is a site at which the detection system binds.

14. The diagnostic marker of claim 13, wherein $X^-$ comprises at least one member selected from the group consisting of halogen ion, acetate ion, perchlorate ion, and carbonate ion.

15. A diagnostic marker, comprising:

a detection system; and a fluorescent functional group that is bound to the detection system and represented by the following formula:

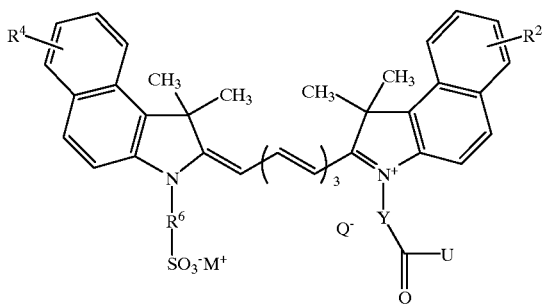

wherein $R^4$ and $R^5$ are independently selected from the group consisting of hydrogen, alkyl group, alkoxy group, and sulfonate group; $R^6$ is an alkylene group; $M^+$ is an alkali metal group; $Q^-$ is selected from the group consisting of halogen ion, perchlorate ion, and thiocyanate ion; Y is a $C_1$–$C_{10}$ alkylene group or a $C_1$–$C_{10}$ alkylene group containing at least one atom selected from the group consisting of oxygen, nitrogen, and sulfur; and U is a site at which the detection system binds.

16. A compound represented by the following formula:

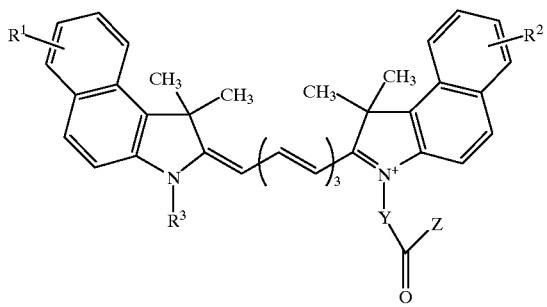

wherein $R^1$ and $R^2$ are independently selected from the group consisting of hydrogen, alkyl group, aryl group, alkoxy group, and sulfonic acid group; $R^3$ is selected from the group consisting of alkyl group, sulfonic acid-alkyl group, and amino-substituted alkyl group; and Z is selected from the group consisting of the following:

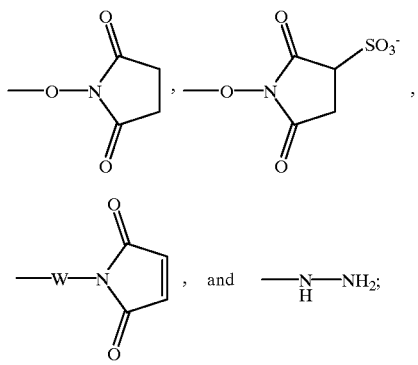

W and Y are independently a $C_1$–$C_{10}$ alkylene group or a $C_1$–$C_{10}$ alkylene group containing at least one atom selected from the group consisting of oxygen, nitrogen, and sulfur.

17. A method comprising reacting a detection system with the compound of claim 16 to form a fluorescent labelling agent.

18. A method for preparing the diagnostic marker of claim 1, which comprises reacting the compound of claim 16 with a detection system.

19. A compound represented by the following formula:

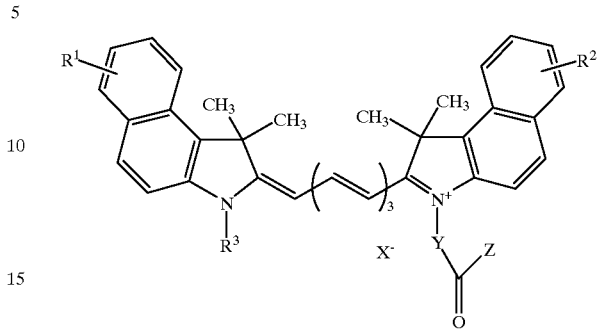

wherein $R^1$ and $R^2$ are independently selected from the group consisting of hydrogen, alkyl group, aryl group, alkoxy group, and sulfonic acid group; $R^3$ is selected from the group consisting of alkyl group, sulfonic acid-alkyl group, and amino-substituted alkyl group; $X^-$ is an anion; and Z is selected from the group consisting of the following:

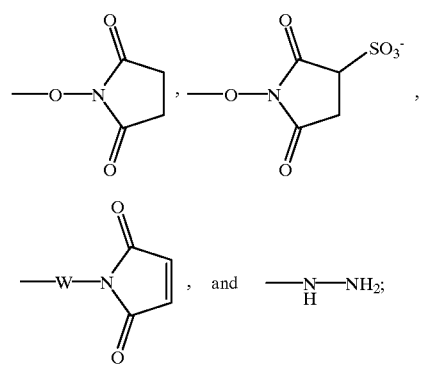

W and Y are independently a $C_1$–$C_{10}$ alkylene group or a $C_1$–$C_{10}$ alkylene group containing at least one atom selected from the group consisting of oxygen, nitrogen, and sulfur.

20. A method comprising reacting a detection system with the compound of claim 19 to form a fluorescent labelling agent.

21. A method for preparing the diagnostic marker of claim 13, which comprises reacting the compound of claim 19 with a detection system.

22. A compound represented by the following formula:

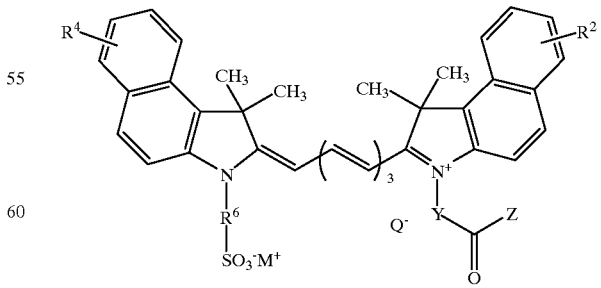

wherein $R^4$ and $R^5$ are independently selected from the group consisting of hydrogen, alkyl group, alkoxy group, and sulfonate group; $R^6$ is an alkylene group; $M^-$ is an alkali metal group; Q⁻ is selected from the group consisting of halogen ion, perchlorate ion, and thiocyanate ion; and Z is selected from the group consisting of the following:

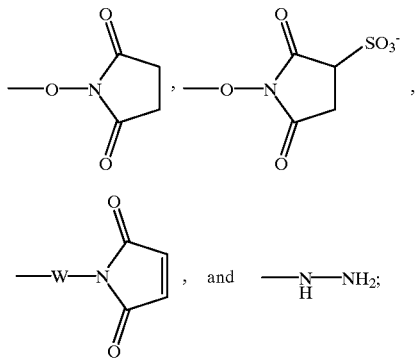

W and Y are independently a $C_1$–$C_{10}$ alkylene group or a $C_1$–$C_{10}$ alkylene group containing at least one atom selected from the group consisting of oxygen, nitrogen, and sulfur.

23. A method comprising reacting a detection system with the compound of claim 22 to form a fluorescent labelling agent.

24. A method for preparing the diagnostic marker of claim 15 which comprises reacting the compound of claim 22 with a detection system.

* * * * *